(12) United States Patent
Byrnes et al.

(10) Patent No.: US 10,130,727 B1
(45) Date of Patent: Nov. 20, 2018

(54) SYSTEMS AND METHODS FOR OPERATING A LIGHT SYSTEM

(71) Applicant: The Boeing Company, Chicago, IL (US)

(72) Inventors: Scott T. Byrnes, Everett, WA (US); Kevin S. Callahan, Everett, WA (US); Alyson M. Bonk, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/633,142

(22) Filed: Jun. 26, 2017

(51) Int. Cl.
*A61L 2/10* (2006.01)
*A61L 2/24* (2006.01)
*H05B 37/02* (2006.01)

(52) U.S. Cl.
CPC ........ *A61L 2/10* (2013.01); *A61L 2/24* (2013.01); *A61L 2202/14* (2013.01); *A61L 2202/25* (2013.01); *H05B 37/0227* (2013.01)

(58) Field of Classification Search
CPC .......... A61L 2/10; A61L 2/24; A61L 2202/14; A61L 2202/25
See application file for complete search history.

(56) References Cited

U.S. PATENT DOCUMENTS

| | | | |
|---|---|---|---|
| 9,623,133 B2 | 4/2017 | Childress et al. | |
| 9,783,974 B1 | 10/2017 | Tillotson | |
| 2010/0193629 A1 | 8/2010 | Breit et al. | |
| 2013/0330235 A1* | 12/2013 | Stibich | A61L 2/24 422/105 |
| 2016/0195427 A1 | 7/2016 | Vance et al. | |
| 2016/0220716 A1 | 8/2016 | Childress et al. | |
| 2016/0250362 A1 | 9/2016 | Mackin | |
| 2017/0107659 A1 | 4/2017 | Hills | |
| 2017/0283062 A1 | 10/2017 | Childress | |
| 2017/0283092 A1 | 10/2017 | Brown et al. | |
| 2017/0284076 A1 | 10/2017 | Jensen | |

OTHER PUBLICATIONS

Co-pending U.S. Appl. No. 15/237,710, filed Aug. 16, 2016.
Co-pending U.S. Appl. No. 15/241,438, filed Aug. 19, 2016.
Co-pending U.S. Appl. No. 15/245,251, filed Aug. 24, 2016.
Co-pending U.S. Appl. No. 15/259,685, filed Sep. 8, 2016.

(Continued)

*Primary Examiner* — Eliza Osenbaugh-Stewart
(74) *Attorney, Agent, or Firm* — McDonnell Boehnen Hulbert & Berghoff LLP

(57) ABSTRACT

In an example, a light-control system includes UV light sources for emitting UV light when activated, a power sensor for measuring an amount of power available, and an activation-control system. The activation-control system can: (a) determine a subset of the UV light sources that are ready to be activated, (b) indicate, in a queue, each UV light source of the subset, (c) arrange, in the queue and based on a hierarchy, the subset in a sequence, and (d) activate, in the sequence, each UV light source of the subset by: (i) determining an amount of power required to activate a next UV light source in the sequence, (ii) determining when the amount of power available is equal to or greater than the amount of power required, (iii) responsively activating the next UV light source in the sequence, and (iv) repeating acts (i)-(iii) until all of the subset has been activated.

20 Claims, 5 Drawing Sheets

(56) References Cited

OTHER PUBLICATIONS

Co-pending U.S. Appl. No. 15/271,349, filed Sep. 21, 2016.
Co-pending U.S. Appl. No. 15/273,814, filed Sep. 23, 2016.
Co-pending U.S. Appl. No. 15/632,968, filed Jun. 26, 2017.
Co-pending U.S. Appl. No. 15/633,028, filed Jun. 26, 2017.
Co-pending U.S. Appl. No. 15/633,085, filed Jun. 26, 2017.
Co-pending U.S. Appl. No. 15/633,121, filed Jun. 26, 2017.

* cited by examiner

SYSTEMS AND METHODS FOR OPERATING A LIGHT SYSTEM

FIELD

The present disclosure generally relates to systems and methods for light systems, and more particularly to systems and methods for operating ultraviolet (UV) light sources to disinfect an environment.

BACKGROUND

Pathogens may be spread between humans, between animals, or between humans and animals in many different ways. Consequently, there is an increasing need for the disinfection of public environments. One approach for disinfecting an environment involves irradiating the environment with ultraviolet (UV) light using UV light sources. However, in some instances, the power required by the UV light sources to achieve a target level of antimicrobial efficacy of the UV lights may exceed the power that is supplied by a power source and/or an electrical infrastructure in the environment.

SUMMARY

In an example, a light control system is described. The light control system includes a plurality of UV light sources. Each UV light source is configured to emit UV light when activated. The light control system also includes a power sensor configured to measure an amount of power available to activate the plurality of UV light sources, and an activation control system in communication with the power sensor.

The activation control system is configured to: (a) determine a subset of the plurality of UV light sources that are ready to be activated, (b) indicate, in a queue stored in a data storage unit, each UV light source of the subset, (c) arrange, in the queue and based on a hierarchy, the subset of the plurality of UV light sources in a sequence, and (d) activate, in the sequence indicated by the queue, each UV light source of the subset by performing a plurality of acts. The acts include: (i) determining an amount of power required to activate a next UV light source in the sequence, (ii) determining when the measured amount of power available to activate the plurality of UV light sources is equal to or greater than the amount of power required to activate the next UV light source in the sequence, (iii) responsive to determining that the amount of power available is equal to or greater than the amount of power required, activating the next UV light source in the sequence, and (iv) repeating acts (i)-(iii) until all of the subset of UV light sources in the queue have been activated.

In another example, a method of operating a plurality of UV light sources is described. The method includes determining a subset of the plurality of UV light sources that are ready to be activated. The method also includes indicating, in a queue stored in a data storage unit, each UV light source of the subset. The method further includes arranging, in the queue and based on a hierarchy, the subset of the plurality of UV light sources in a sequence. Additionally, the method includes measuring an amount of power available to activate the plurality of UV light sources and activating, in the sequence indicated by the queue, each UV light source of the subset by performing a plurality of acts. The plurality of acts include: (i) determining an amount of power required to activate a next UV light source in the sequence, (ii) determining when the measured amount of power available to activate the plurality of UV light sources is equal to or greater than the amount of power required to activate the next UV light source in the sequence, (iii) responsive to determining that the amount of power available is equal to or greater than the amount of power required, activating the next UV light source in the sequence to cause the next UV light source to emit UV light, and (iv) repeating acts (i)-(iii) until all of the subset of UV light sources in the queue have been activated.

In another example, a method of operating a plurality of UV light sources is described. The method includes determining that a first UV light source is ready to be activated, determining that a second UV light source is ready to be activated, measuring an amount of power available to activate the first UV light source and the second UV light source, determining an amount of power required to simultaneously activate the first UV light source and the second UV light source, and determining whether (i) the amount of power available is greater than or equal to the amount of power required or (ii) the amount of power available is less than the amount of power required.

If the amount of power available is greater than or equal to the amount of power required, then the method includes simultaneously activating the first UV light source and the second UV light source to cause the first UV light source and the second UV light source to emit UV light. Whereas, if the amount of power is less than the amount of power required, then the method includes performing a plurality of acts. The plurality of acts include determining, based on a hierarchy, a sequence for activating the first UV light source and the second UV light source. The plurality of acts also include responsive to determining the sequence, activating the first UV light source and the second UV light source in the sequence one UV light source at a time.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

DETAILED DESCRIPTION

Figure 1:
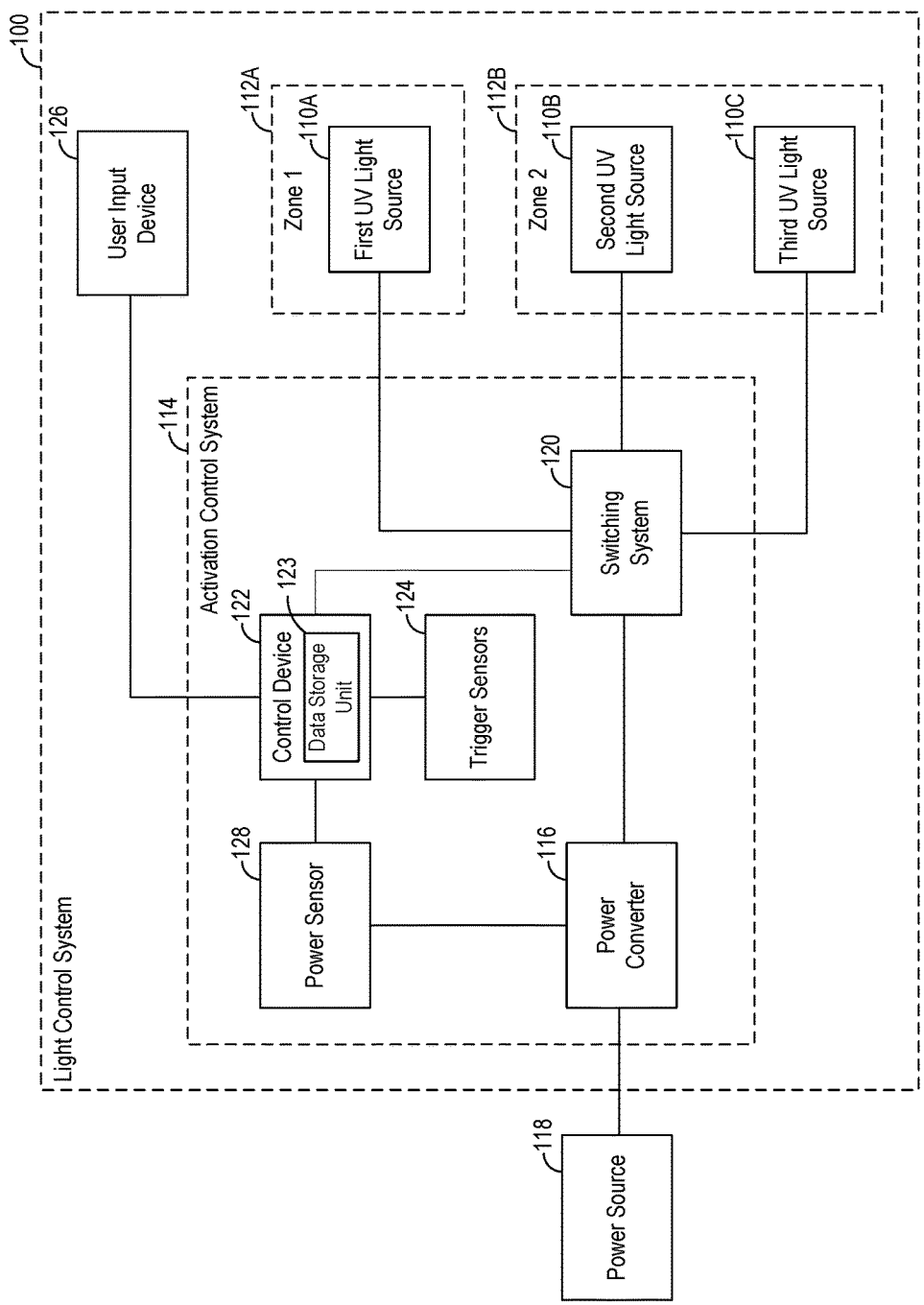
FIG. 1 illustrates a simplified block diagram of a light control system according to an example embodiment.

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

The systems and methods of the present disclosure provide light control systems and methods for operating UV light sources to disinfect an environment. When activated during an activation cycle, the UV light sources emit UV light, which can kill and/or disable microorganisms such as bacteria, viruses, molds, and/or other pathogens. For example, when microorganisms are exposed to a sufficiently high dose of UV light, the UV light can damage nucleic acids and/or disrupt the deoxyribonucleic acid (DNA) of the microorganisms, rendering the microorganisms unable to carry out cellular functions and infect people.

The antimicrobial efficacy of the UV light during the activation cycle is related to factors such as, for instance, the length of time a microorganism is exposed to the UV light (i.e., the "exposure time"), the intensity of the UV light, and the wavelength of the UV light. As one example, the antimicrobial efficacy of the UV light at a particular wavelength can be specified as a UV dose, which can be determined based on an equation having the general form of:

$$\text{UV dose} = \text{UV light intensity} \times \text{exposure time} \quad (\text{eq. 1})$$

where the UV dose is specified in mWs/cm$^2$, the UV light intensity is specified in mW/cm$^2$ at a predetermined distance (e.g., one meter) from the UV light source, and the exposure time is specified in seconds.

Because each UV light source converts electrical power into the UV light, the UV light source may require at least a threshold amount of power to emit the UV light at the intensity and/or for the exposure time providing the target level of antimicrobial efficacy. The threshold amount of power required to emit the UV light at the target level of antimicrobial efficacy may be based on characteristics of the UV light source such as, for example, a type of UV light source, and/or a size of the UV light source.

In a limited-power environment, a power source and/or an electrical distribution system may provide a power that is insufficient by itself for simultaneously activating multiple UV light sources to emit the UV light at the target level of antimicrobial efficacy. In one example, the UV light sources can be coupled to a power source, which is configured to generate a power that is less than the threshold amount of power required by the UV light sources to simultaneously emit the UV light at the target level of antimicrobial efficacy. For instance, the UV light sources can be installed in an environment in which it is desirable to reduce (or minimize) the size and/or weight of the power source.

In another example, the power source may be configured to generate a sufficient amount of power, but an electrical distribution system may supply portions of the generated power to other systems as well such that only an insufficient portion of the power is available to the UV light sources. For instance, a vehicle can have an electrical distribution system that provides specific portions of a power supplied by a power source to various subsystems of the vehicle in accordance with a power budget. In this way, each subsystem receives an amount of power that is sufficient to meet its needs. A challenge is presented, however, when the vehicle is to be retrofitted with the UV light sources as the power requirements of the UV light sources may not have been taken into consideration when the power budget and electrical distribution system were designed.

The example systems and methods described herein can beneficially overcome challenges to operating a plurality of UV light sources when an amount of power that is available is less than an amount of power that is required to simultaneously activate the UV light sources. Within examples, a light control system can include a plurality of UV light sources and an activation control system. When multiple UV light sources are ready to be activated and the amount of power is insufficient to simultaneously activate the UV light sources, the activation control system can manage a series of activations of the UV light sources based on a hierarchy, which provides a sequence for activating the UV light sources. As described in detail below, the activation control system can implement the hierarchy as a set of rules based on one or more factors relating to the UV light sources, the environments in which the UV light sources are located, and/or the power available to activate the UV light sources.

Referring now to FIG. 1, a light control system 100 is depicted according to an example embodiment. The light control system 100 includes a plurality of UV light sources 110A-110C. In FIG. 1, the UV light sources 110A-110C include a first UV light source 110A, a second UV light source 110B, and a third UV light source 110C. Although three UV light sources 110A-110C are shown in FIG. 1, the light control system 100 can include a lesser or greater quantity of UV light sources 110A-110C in other examples.

When activated, each UV light source 110A-110C can emit UV light to disinfect an environment in which the UV light source 110A-110C is located. For instance, as shown in FIG. 1, the first UV light source 110A is in a first zone 112A, and the second UV light source 110B and the third UV light source 110C are in a second zone 112B. The zones 112A-112B can be in any environment, which can benefit from being disinfected by the UV light sources 110A-110C. For instance, the light control system 100 can be in a vehicle (e.g., an aircraft, a watercraft, a train, an automobile, and/or a spacecraft), a medical environment (e.g., a hospital, a doctor office, and/or other healthcare facility), a restaurant, an office, and/or a household.

In one implementation, the light control system 100 is located on a vehicle having a plurality of lavatories. In this implementation, the first zone 112A can be in a first lavatory of the vehicle and the second zone 112B can be in a second lavatory of the vehicle. Accordingly, as described below, the light control system 100 can control activation of multiple UV light sources 110A-110C within the same zone and/or within different zones. Although two zones 112A-112B are shown in FIG. 1, the light control system 100 can include a lesser or greater quantity of zones 112A-112B in other examples. In general, the light control system 100 can include a plurality of UV light sources 110A-110C distributed over one or more zones 112A-112B.

As examples, each UV light source 110A-110C can include one or more excimer bulbs, mercury-vapor lamps, and/or light emitting diodes (LEDs). More generally, the UV light sources 110A-110C can be light sources that each emit the UV light at a wavelength within the UV spectrum (i.e., between approximately 10 nanometers (nm) and approximately 400 nm). In some implementations, the UV light sources 110A-110C can be light sources that each emit UV light at a wavelength within the far-UV spectrum (e.g., between approximately 190 nm and approximately 240 nm). For instance, in one implementation, the UV light sources 110A-110C can be light sources that each emit the UV light at a wavelength of approximately 222 nm. By emitting the UV light at a wavelength in the far-UV spectrum, the UV light sources 110A-110C can more rapidly disinfect the environment than by emitting the UV light at other wavelengths in the UV spectrum.

Within examples, each UV light source 110A-110C can be activated during an activation cycle at an intensity and/or for an exposure time that achieve a target level of antimicrobial efficacy. In one example, the target level of antimicrobial efficacy is a UV dose of approximately 10 mWs/cm². In additional or alternative examples, the target level of antimicrobial efficacy can be a UV dose between approximately 2 mWs/cm² and approximately 500 mWs/cm². Different microorganisms may have different abilities to withstand exposure to the UV light. In some implementations, the target level of antimicrobial efficacy can be based on a target microorganism-kill rate for one or more types of microorganisms that are targeted for disinfection by the light control system. As an example, the targeted micro-organism kill rate can be approximately 80% to approximately 99.99%. For instance, the targeted microorganism-kill rate can be approximately 80%, approximately 90%, approximately 95%, approximately 99%, approximately 99.9%, and/or approximately 99.99% of the one or more target microorganisms irradiated by the UV dose.

As shown in FIG. 1, the light control system 100 also includes an activation control system 114 for controlling activations and/or deactivations of the UV light sources 110A-110C. The activation control system 114 can include a power converter 116, which receives an input power from a power source 118. As an example, the power source 118 can provide the input power as an alternating current (AC) power. In one implementation, the power source 118 can provide the input power as a three-phase AC power with a voltage of approximately 115 volts (V) and a frequency of approximately 360 Hertz (Hz) to approximately 800 Hz. For instance, in a vehicle, the power source 118 can include an engine turbine that generates electrical energy and an electrical distribution system that provides the generated electrical energy to the light control system 100 in the form of the input power. Other example power sources 118 are also possible.

The power converter 116 converts the input power to a supply power. Within examples, the supply power can have a different AC waveform than the input power. That is, a value of the electrical parameter of the supply power can be different than a value of the electrical parameter of the input power. As examples, the electrical parameter can be a frequency, a voltage, a current, and/or a wattage of the AC waveform of the input power and the supply power. In this way, the power converter 116 can condition the input power received from the power source 118 to efficiently operate the UV light sources 110A-110C, for example, at a target level of antimicrobial efficacy (e.g., at an intensity and/or for an exposure time corresponding to the target level of antimicrobial efficacy).

The activation control system 114 can control a flow of the supply power to one or more of the UV light sources 110A-110C to selectively activate and/or deactivate the UV light source(s) 110A-110C. For example, in FIG. 1, the activation control system 114 includes a switching system 120 coupled to the power converter 116 and the UV light sources 110A-110C. The switching system 120 can selectively couple each of the UV light sources 110A-110C to the supply power received from the power converter 116. For instance, to activate one or more of the UV light sources 110A-110C, the switching system 120 can couple the one or more UV light sources 110A-110C to the supply power and decouple a remainder of the UV light sources 110A-110C from the supply power. As examples, the switching system 120 can include one or more single pole single throw switches, a single pole double throw switches, a transistors, and/or diodes to facilitate independently and selectively coupling and decoupling the UV light sources 110A-110C as described herein.

In one implementation, the switching system 120 can be actuated between a plurality of states such that, in each state, the switching system 120 can couple and/or decouple a respective combination of the UV light sources 110A-110C to the supply power. For example, in FIG. 1, the switching system 120 can have (i) a first state in which the switching system 120 couples none of the UV light sources 110A-110C to the supply and decouples all of the UV light sources 110A-110C from the supply power, (ii) a second state in which the switching system 120 couples the first UV light source 110A to the supply power and decouples the remainder of the UV light sources 110B-110C from the supply power, (iii) a third state in which the switching system 120 couples the second UV light source 110B to the supply power and decouples the remainder of the UV light sources 110A, 110C from the supply power, (iv) a fourth state in which the switching system 120 couples the third UV light source 110C to the supply power and decouples the remainder of the UV light sources 110A-110B from the supply power, (v) a fifth state in which the switching system 120 couples the first UV light source 110A and the second UV light source 110B to the supply power and decouples the remainder of the UV light sources 110B from the supply power, (vi) a sixth state in which the switching system 120 couples the second UV light source 110B and the third UV light source 110C to the supply power and decouples the remainder of the UV light sources 110A from the supply power, (vii) a seventh state in which the switching system 120 couples the first UV light source 110A and the third UV light source 110C to the supply power and decouples the remainder of the UV light sources 110B from the supply power, and (viii) an eighth state in which the switching system 120 couples all of the UV light sources 110A-110C to the supply power and decouples none of the UV light sources 110A-110C from the supply power. In other examples, the switching system 120 can have a lesser or greater quantity of states.

The switching system 120 can be in communication with a control device 122. The control device 122 can transmit a control signal to the switching system 120 to control the operation of the switching system 120. For instance, the control device 122 can transmit a control signal to actuate the switching system 120 from one of the states (i.e., the first to eighth states) to another of the states to cause the switching system 120 to selectively couple one or more of the UV light sources 110A-110C to the supply power and/or decouple the remainder of the UV light sources 110A-110C from the supply power.

In general, the control device 122 is a computing device that is configured to control operation of the light control system 100. As such, the control device 122 can be implemented using hardware, software, and/or firmware. For example, the control device 122 can include one or more processors and a non-transitory computer readable medium (e.g., a data storage unit 123 in the form of volatile and/or non-volatile memory) that stores machine language instructions or other executable instructions. The instructions, when executed by the one or more processors, cause the light control system 100 to carry out the various operations described herein. The control device 122, thus, can receive data (including data indicated by the sensor signals and/or trigger-sensor signals described below) and store the data in memory as well.

The control device 122 can transmit the control signals to the switching system 120 responsive to the control device 122 determining that one or more of the UV light sources 110A-110C is ready to be activated. In an example, for each UV light source 110A-110C, the control device 122 can determine that the UV light source 110A-110C is ready to be activated based, at least in part, on one or more trigger conditions. For instance, as shown in FIG. 1, the activation control system 114 can include one or more trigger sensors 124 in communication with the control device 122. The one or more trigger sensors 124 can detect the trigger condition(s) and responsively generate a trigger-sensor signal indicating that the trigger condition(s) were detected. The control device 122 can (i) receive the trigger-sensor signal indicating that the trigger condition was detected, (ii) determine, based on the trigger-sensor signal, that one or more criteria are met, and (iii) responsive to the determination that the one or more criteria are met, transmit a control signal to the switching system 120 activate one or more of the UV light sources 110A-110C.

In an example, the trigger sensor(s) 124 can include a motion sensor, an occupancy sensor, a thermal sensor, an open/close sensor, an infrared sensor device, an ultrasonic sensor device, a floor pressure sensor, and/or other types of sensors. Each trigger sensor 124 can correspond to at least one of the UV light sources 110A-110C. As such, each trigger sensor 124 can detect the trigger condition(s) relating to the at least one UV light source 110A-110C corresponding to the trigger sensor 124.

For instance, in one implementation, the trigger sensors 124 can include a first trigger sensor that detects trigger condition(s) relating to the first UV light source 110A, a second trigger sensor that detects trigger condition(s) relating to the second UV light source 110B, and a third trigger sensor that detect trigger condition(s) relating to the third UV light source 110C. In an alternative implementation, the trigger sensors 124 can include a first trigger sensor that detects trigger condition(s) relating to the first UV light source 110A, and a second trigger sensor that detects trigger condition(s) relating to the second UV light source 110B and the third UV light source 110C. The control device 122 can store an association between the trigger sensors 124 and the UV light sources 110A-110C.

In an example in which each UV light source 110A-110C is located in a lavatory of a vehicle, the trigger condition(s) detected by the trigger sensor(s) 124 corresponding to the UV light source 110A-110C can include a door of the lavatory being opened, the door of the lavatory being closed, the lavatory being occupied, and/or the lavatory being unoccupied. Additionally, for example, the one or more criteria that is used by the control device 122 to determine whether to activate each UV light source 110A-110C can include one or more criterion such as the door of the lavatory being closed, the lavatory being unoccupied, the lavatory having been occupied a predetermined number of times since a pervious activation of the UV light source 110A-110C, and/or a predetermined amount of time having passed since the previous activation of the UV light source 110A-110C.

Additionally, as shown in FIG. 1, the control device 122 can be in communication with a user input device 126, which can facilitate activating the UV light sources 110A-110C. The user input device 126 can receive a user input indicating a request to activate one or more of the UV light sources 110A-110C, and transmit an input signal to the control device 122 to cause the control device 122 to determine that the UV light source(s) 110A-110C indicated by the input signal are ready to be activated. As examples, the user input device 126 can include one or more touchscreens, buttons, keypads, keyboards, computer mice, and/or voice-controlled input devices. By activating the UV light sources 110A-110C based on the user input, the UV light sources 110A-110C can be activated in an on-demand manner. This may be advantageous, for example, in a scenario in which a person observes a condition in the first zone 112A and/or the second zone 112B that may benefit from being disinfected by the UV light source(s) 110A-110C in that zone 112A, 112B.

As noted above, the control device 122 can actuate the switching system 120 to activate and/or deactivate the UV light sources 110A-110C. Each UV light source 110A-110C may require a respective amount of power to activate the UV light source 110A-110C and emit the UV light at a target level of efficacy. A challenge is thus encountered when an amount of power that is available is less than an amount of power that is required to simultaneously activate the UV light sources 110A-110C, which are ready to be activated.

To overcome such challenges, the activation control system 114 can manage activations of the UV light sources 110A-110C based on a hierarchy, which provides a sequence for activating the UV light sources 110A-110C. Within examples, the control device 122 can (i) determine a subset of the UV light sources 110A-110C that are ready to be activated, (ii) indicate, in a queue stored in the data storage unit 123, each UV light source 110A-110C of the subset, (iii) arrange, in the queue and based on the hierarchy, the subset of the UV light sources 110A-110C in a sequence, and (iv) activate, in the sequence indicated by the queue, each UV light source 110A-110C of the subset.

The control device 122 can determine the subset of the UV light sources 110A-110C, which are ready to be activated, based on the trigger-sensor signals and/or user input signals as described above. The UV light sources 110A-110C of the subset can vary over time as the UV light sources 110A-110C become ready to be activated and/or as activations of the light sources 110A-110C are completed. As such, the subset of the UV light sources 110A-110C can include all of the UV light sources 110A-110C at a first time, and the subset can include less than all of the UV light sources 110A-110C at a second time.

In an example, the sequence can be indicated by a plurality of index positions in the queue such that the control device 122 can activate the UV light sources 110A-110C in an order from a first of the index positions to a last of the index positions. In one implementation, each of the UV light sources 110A-110C in the queue is assigned to a respective one of the index positions. This may be beneficial in instances in which the amount of power that is expected to be available is sufficient to activate only one of the UV light sources 110A-110C at a time.

In additional or alternative implementations, each index position can include one or more of the UV light sources 110A-110C in the queue. For instance, one of the index positions in the queue can include two or more UV light sources 110A-110C in the queue. This may be beneficial in instances in which the power that is expected to be available to activate the UV light sources 110A-110C is likely to be sufficient to simultaneously activate the two or more UV light sources 110A-110C at the single index position in the queue. As described in further detail below, in some examples, the activation control system 114 can evaluate the amount of power available and the amount of power required to activate the UV light sources 110A-110C to arrange the UV light sources 110A-110C in the index positions of the sequence.

The activation control system 114 can activate each UV light source 110A-110C of the subset, on an index position by index position basis, as power becomes available to activate the UV light sources 110A-110C in the sequence. For example, to activate each UV light source 110A-110C of the subset, the control device 122 can perform a plurality of acts including: (i) determining an amount of power required to activate a next UV light source 110A-110C in the sequence, (ii) determining when a measured amount of power available to activate the UV light sources 110A-110C is equal to or greater than the amount of power required to activate the next UV light source 110A-110C in the sequence, (iii) responsive to determining that the amount of power available is equal to or greater than the amount of power required, activating the next UV light source 110A-110C in the sequence, and (iv) repeating acts (i)-(iii) until all of the subset of UV light sources 110A-110C in the queue have been activated.

To measure the amount of power available to activate the UV light sources 110A-110C, the light control system 100 includes a power sensor 128. As shown in FIG. 1, the power sensor 128 is in communication with the control device 122. Additionally, the power sensor 128 can sense the input power provided by the power source 118 to the power converter 116 and/or the supply power provided by the power converter 116 to the switching system 120 to determine the amount of power available to activate the UV light sources 110A-110C. Based on the sensed input power and/or supply power, the power sensor 128 can provide a power-sensor signal to the control device 122 indicating the measured amount of power available to activate the UV light sources 110A-110C.

As one example, the power sensor 128 can include a current sensor that can measure the current of the input power and/or the supply power, and determine the amount of power available based on the measured current and a known voltage of the input power and/or the supply power. As another example, the power sensor 128 can include a current sensor and a voltage sensor, and the power sensor 128 can determine the amount of power from the measured current and the measured voltage. As further examples, the power sensor 128 can include one or more analog wattmeters and/or digital wattmeters.

The control device 122 can store, for each UV light source 110A-110C, information relating to the amount of power required to activate the UV light source 110A-110C. In one example, the amount of power required to activate each UV light source 110A-110C can be based on one or more of a size of the UV light source 110A-110C, an intensity at which the UV light source 110A-110C emits UV light, an exposure time for activating the UV light source 110A-110C, and/or a power required to activate the UV light source 110A-110C (e.g., at a target antimicrobial efficacy for the UV light source 110A-110C). In one implementation, the amount of power required to activate each UV light source 110A-110C can be fixed. In an additional or alternative example, the amount of power required to activate each UV light source 110A-110C can by adjusted, for instance, based on user input provided via the user input device 126.

Within examples, the control device 122 can implement the hierarchy as a set of rules based on one or more factors. As examples, the one or more factors can include a location of each UV light source 110A-110C, a size of each UV light source 110A-110C, an operational status of a vehicle in which each UV light source 110A-110C is located, an amount of time since a last activation of each UV light source 110A-110C, a frequency of usage of each UV light source 110A-110C, a frequency of usage of a respective environment (e.g., the zones 112A, 112B) disinfected by each UV light source 110A-110C, and/or the amount of power required to activate each UV light source 110A-110C.

In one example, the UV light sources 110A-110C can be on a vehicle. In this example, the UV light sources 110A-110C can be located at one or more lavatories, food storage areas, trash receptacles, galleys, seat-back tray tables, armrests, head rests, coat closets, and/or door handles of the vehicle. Accordingly, in some examples, the hierarchy can be configured to prioritize the UV light sources 110A-110C based, at least in part, on such locations of the UV light sources 110A-110C.

As further examples, the locations of the UV light sources 110A-110C can be differentiated by whether the UV light sources 110A-110C are located in a front portion of the vehicle, a middle portion of the vehicle, and/or a rear portion of the vehicle. Further, the hierarchy can be based on how many UV light sources 110A-110C are at the same location and/or a relative distance between the UV light sources 110A-110C. For instance, in FIG. 1, the hierarchy can prioritize activating the second UV light source 110B and the third UV light source 110C over activating the first UV light source 110A (or vice versa) because the second UV light source 110B and the third UV light source 110C are both in the second zone 112B.

In another example, the UV light sources 110A-110C can be in a plurality of lavatories of an aircraft. In this example, for each UV light source 110A-110C, the location of the UV light source 110A-110C can include a class of a cabin in which the UV light source 110A-110C is located (e.g., a first class cabin, a business class cabin, and/or an economy class cabin). In one implementation, the hierarchy can be configured to (i) prioritize the UV light source(s) 110A-110C in the economy class cabin over the UV light source(s) 110A-110C in the business class cabin and the first class cabin, and/or (ii) prioritize the UV light source(s) 110A-110C in the business class cabin over the UV light source(s) 110A-110C in the first class cabin. As the economy class cabin generally includes a greater quantity and/or density of passengers than the other cabins, this configuration of the hierarchy can allow the activation control system 114 to prioritize disinfecting lavatories that are likely to experience relatively heavy usage over disinfecting lavatories that are likely to experience relatively light usage.

In another implementation, the hierarchy can be configured to (i) prioritize the UV light source(s) 110A-110C in the first class cabin over the UV light source(s) 110A-110C in the business class cabin and the economy class cabin, and/or (ii) prioritize the UV light source(s) 110A-110C in the business class cabin over the UV light source(s) 110A-110C in the economy class cabin. This can allow the activation control system 114 to prioritize disinfecting lavatories that service higher fare passengers over disinfecting lavatories that service lower fare passengers.

Also, in an example in which the UV light sources 110A-110C are in an aircraft, the operational status of the vehicle can include a phase of flight of the aircraft. In an implementation in which the hierarchy is based on the phase of flight, the hierarchy can be based on whether the aircraft is in a takeoff, ascent, cruise, descent, final approach, and/or landing operational status. As food and/or beverage service is typically performed while the aircraft is in a cruise operational status, it may be beneficial to prioritize certain UV light sources 110A-110C over other UV light sources 110A-110C depending on whether the aircraft is in the cruise operational status.

As noted above, the hierarchy can additionally or alternatively be based on an amount of time since a last activation of each UV light source 110A-110C and/or a frequency of usage of a respective environment (e.g., the zones 112A, 112B) disinfected by each UV light source 110A-110C. In one implementation, the hierarchy can be configured to prioritize the UV light source(s) 110A-110C that have gone the longest time since the last activation over the UV light source(s) 110A-110C that have been more recently activated. Similarly, the hierarchy can be configured to prioritize the UV light source(s) 110A-110C in more frequently used environments over the UV light source(s) 110A-110C in less frequently used environments. This can help to more rapidly disinfect the environments that are more likely to have a relatively greater need for disinfection.

Also, as noted above, the hierarchy can additionally or alternatively be based on the amount of power required to activate each UV light source 110A-110C. In one implementation, the hierarchy can be configured to sequence the UV light sources 110A-110C in a manner that most efficiently uses the available power to activate the UV light sources 110A-110C in the least amount of time. For instance, if the amount of power available to activate the UV light sources 110A-110C is sufficient to simultaneously activate the second UV light source 110B and the third UV light source 110C, the hierarchy can assign the second UV light source 110B and the third UV light source 110C to a higher index position in the queue than the first UV light source 110A so that two of the UV light sources 110A-110C are activated sooner. Other examples are also possible.

The control device 122 can thus be configured to store data relating to the power requirements of each UV light source 110A-110C, the activation histories of each UV light source 110A-110C, and/or the usage of the environments (e.g., zones 112A, 112B) in which each UV light sources 110A-110C is located. For instance, the control device 122 can determine the frequency of usage of the environments based on the trigger-sensor signals received from the trigger sensors 124. Additionally, for instance, the control device 122 can store in the data storage unit 123 information relating to each UV light source 110A-110C such as, for instance, a size of the UV light source 110A-110C, an intensity at which the UV light source 110A-110C emits UV light, an exposure time for activating the UV light source 110A-110C, and/or a power required to activate the UV light source 110A-110C (e.g., at a target antimicrobial efficacy for the UV light source 110A-110C).

In one example, the hierarchy can be a fixed rule set that does not change. In an alternative example, the hierarchy can by adjusted, for instance, based on user input provided via the user input device 126. Accordingly, the user input device 126 can be configured to receive the user input and transmit an input signal indicative of the user input to the activation control system, and the activation control system 114 can be configured to adjust the hierarchy based on the user input indicated by the input signal.

In operation, the control device 122 of the activation control system 114 can determine that a subset of the UV light sources 110A-110C are ready to be activated (e.g., based on triggers signals provided by the trigger sensors 124 and/or input signals provided by the user input device 126). The activation control system 114 can then determine the amount of power that is available to activate the UV light sources 110A-110C based on the power sensor signal provided by the power sensor 128. The control device 122 can compare the amount of power available to the amount of power required to simultaneously activate the subset of UV light sources 110A-110C.

If the control device 122 determines that the amount of power available is greater than or equal to the amount of power required to simultaneously activate the subset of UV light sources 110A-110C, the activation control system 114 can actuate the switching system 120 to simultaneously activate the subset of UV light sources 110A-110C. Whereas, if the control device 122 determines that the amount of power available is less than the amount of power required to simultaneously activate the subset of UV light sources 110A-110C, the control device 122 can determine a sequence for arranging the subset of UV light sources 110A-110C in the queue.

The control device 122 can then activate, in the sequence indicated by the queue, each UV light source 110A-110C of the subset. To do so, the activation control system 114 can activate each UV light source 110A-110C of the subset, on an index position by index position basis, as power becomes available to activate the UV light sources 110A-110C in the sequence. For example, to activate each UV light source 110A-110C of the subset, the control device 122 can perform a plurality of acts including: (i) determining an amount of power required to activate a next UV light source 110A-110C in the sequence, (ii) determining when a measured amount of power available to activate the plurality of UV light sources 110A-110C is equal to or greater than the amount of power required to activate the next UV light source 110A-110C in the sequence, (iii) responsive to determining that the amount of power available is equal to or greater than the amount of power required, activating the next UV light source 110A-110C in the sequence, and (iv) repeating acts (i)-(iii) until all of the subset of UV light sources 110A-110C in the queue have been activated. After completing the activation of each UV light source 110A-110C, the control device 122 can remove the UV light source 110A-110C from the queue.

In some instances, while activating the UV light sources 110A-110C in the sequence, the control device 122 may determine that an additional UV light source 110A-110C should be added to the subset and the queue. In such instances, the control device 122 can repeat the process of evaluating the available power and arranging the subset in the sequence based on the hierarchy. In other words, the sequence of the UV light sources 110A-110C in the queue may change over time as additional UV light sources 110A-110C become ready to be activated and/or as activations of UV light sources 110A-110C are completed.

Figure 2:
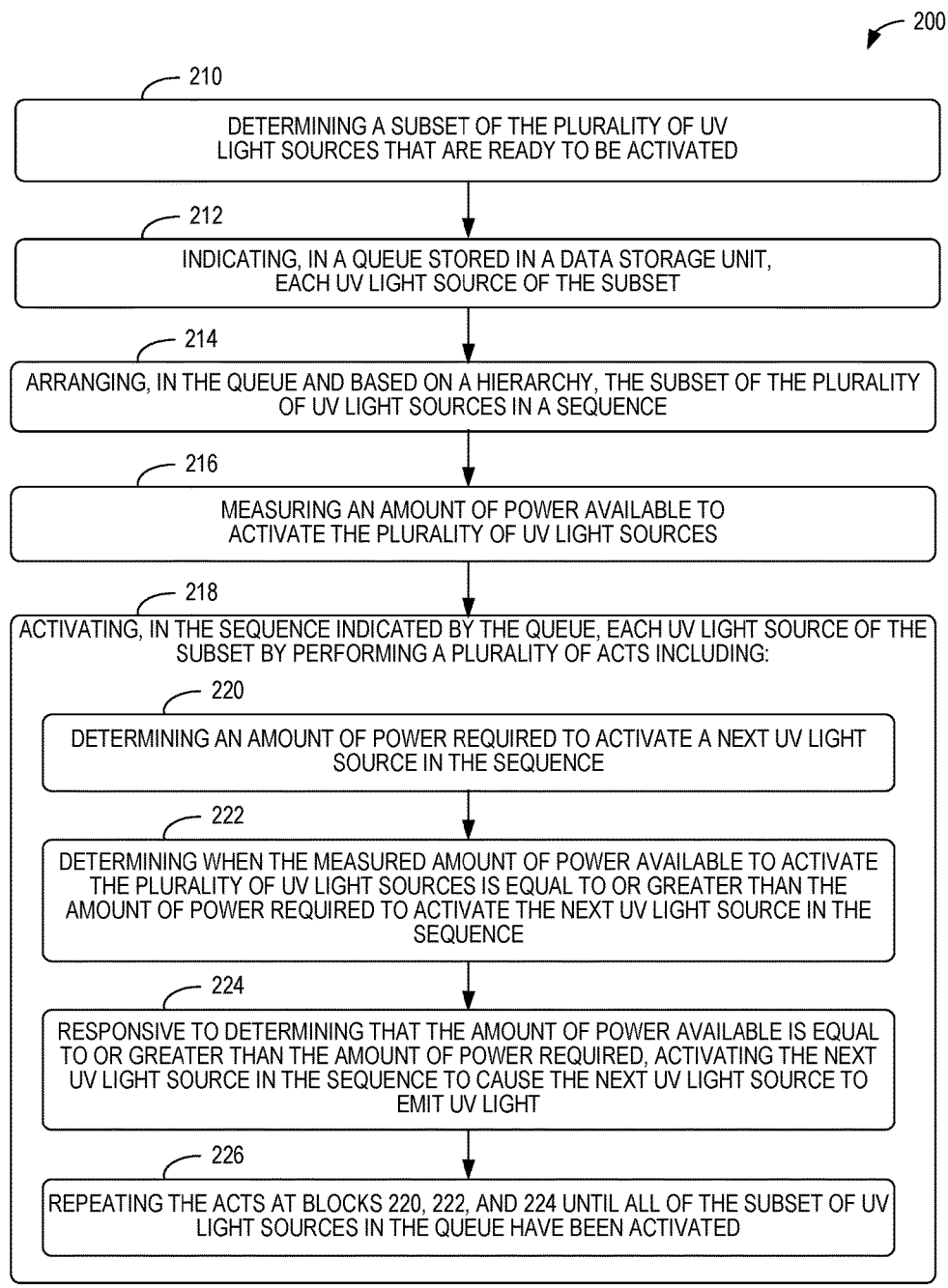
FIG. 2 illustrates a flow chart of an example process for operating a plurality of UV light sources according to an example embodiment.

Referring now to FIG. 2, a flowchart for a process 200 of operating a plurality of UV light sources is illustrated according to an example embodiment. As shown in FIG. 2, at block 210, the process 200 includes determining a subset of the plurality of UV light sources that are ready to be activated. At block 212, the process 200 includes indicating, in a queue stored in a data storage unit, each UV light source of the subset. At block 214, the process 200 includes arranging, in the queue and based on a hierarchy, the subset of the plurality of UV light sources in a sequence. At block 216, the process 200 includes measuring an amount of power available to activate the plurality of UV light sources. At block 218, the process 200 includes activating, in the sequence indicated by the queue, each UV light source of the subset by performing a plurality of acts.

As shown in FIG. 2, the plurality of acts can include: (i) determining an amount of power required to activate a next UV light source in the sequence at block 220, (ii) determining when the measured amount of power available to activate the plurality of UV light sources is equal to or greater than the amount of power required to activate the next UV light source in the sequence at block 222, (iii) responsive to determining that the amount of power available is equal to or greater than the amount of power required at block 222, activating the next UV light source in the sequence to cause the next UV light source to emit UV light at block 224, and (iv) repeating acts (i)-(iii) at blocks 220, 222, and 224 until all of the subset of UV light sources in the queue have been activated at block 226.

Figure 3:
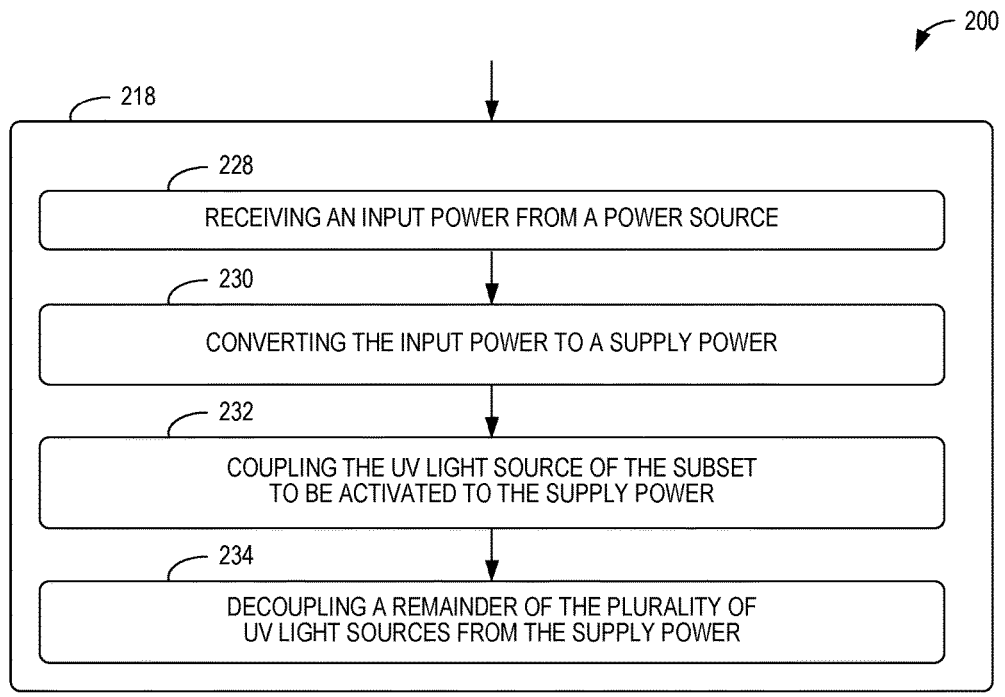
FIG. 3 illustrates a flow chart of an example process for operating a plurality of UV light sources that can be used with the process shown in FIG. 2.
Figure 4:
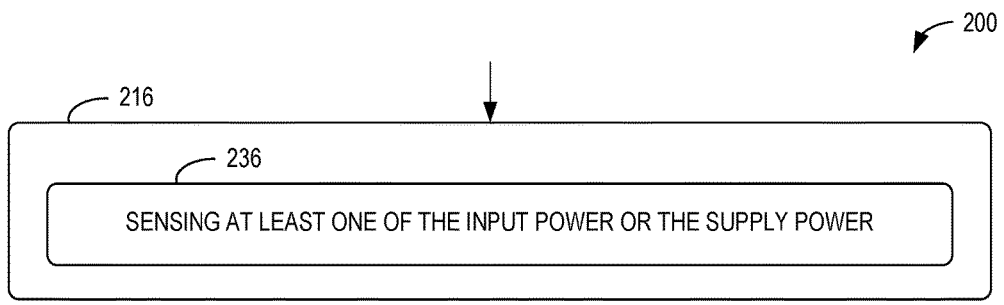
FIG. 4 illustrates a flow chart of an example process for operating a plurality of UV light sources that can be used with the process shown in FIG. 3.

FIGS. 3-6 depict additional aspects of the process according to further examples. As shown in FIG. 3, activating each UV light source of the subset at block 218 can also include receiving an input power from a power source at block 228, converting the input power to a supply power at block 230, coupling the UV light source of the subset to be activated to the supply power at block 232, and decoupling a remainder of the plurality of UV light sources from the supply power at block 234. Also, as shown in FIG. 4, measuring the amount of power available to activate the plurality of UV light sources at block 216 can include sensing at least one of the input power or the supply power at block 236

Figure 5:
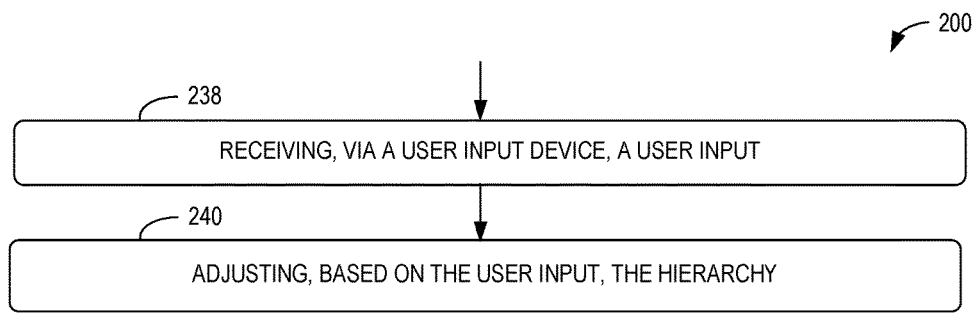
FIG. 5 illustrates a flow chart of an example process for operating a plurality of UV light sources that can be used with the process shown in FIGS. 2-4.
Figure 6:
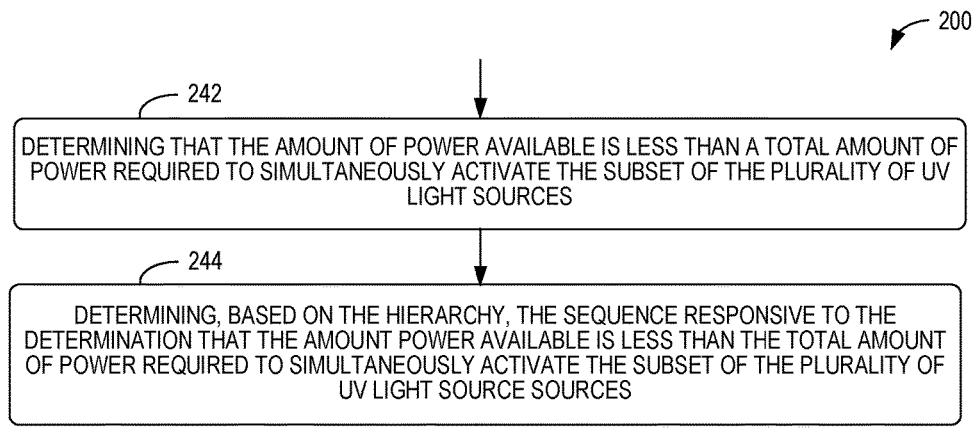
FIG. 6 illustrates a flow chart of an example process for operating a plurality of UV light sources that can be used with the process shown in FIGS. 2-5.

As shown in FIG. 5, the process 200 can include receiving, via a user input device, a user input at block 238 and adjusting, based on the user input, the hierarchy at block 240. As shown in FIG. 6, the process can include determining that the amount of power available is less than a total amount of power required to simultaneously activate the subset of the plurality of UV light sources at block 242. At block 244, the process 200 can include determining, based on the hierarchy, the sequence responsive to the determination that the amount power available is less than the total amount of power required to simultaneously activate the subset of the plurality of UV light source sources.

Figure 7:
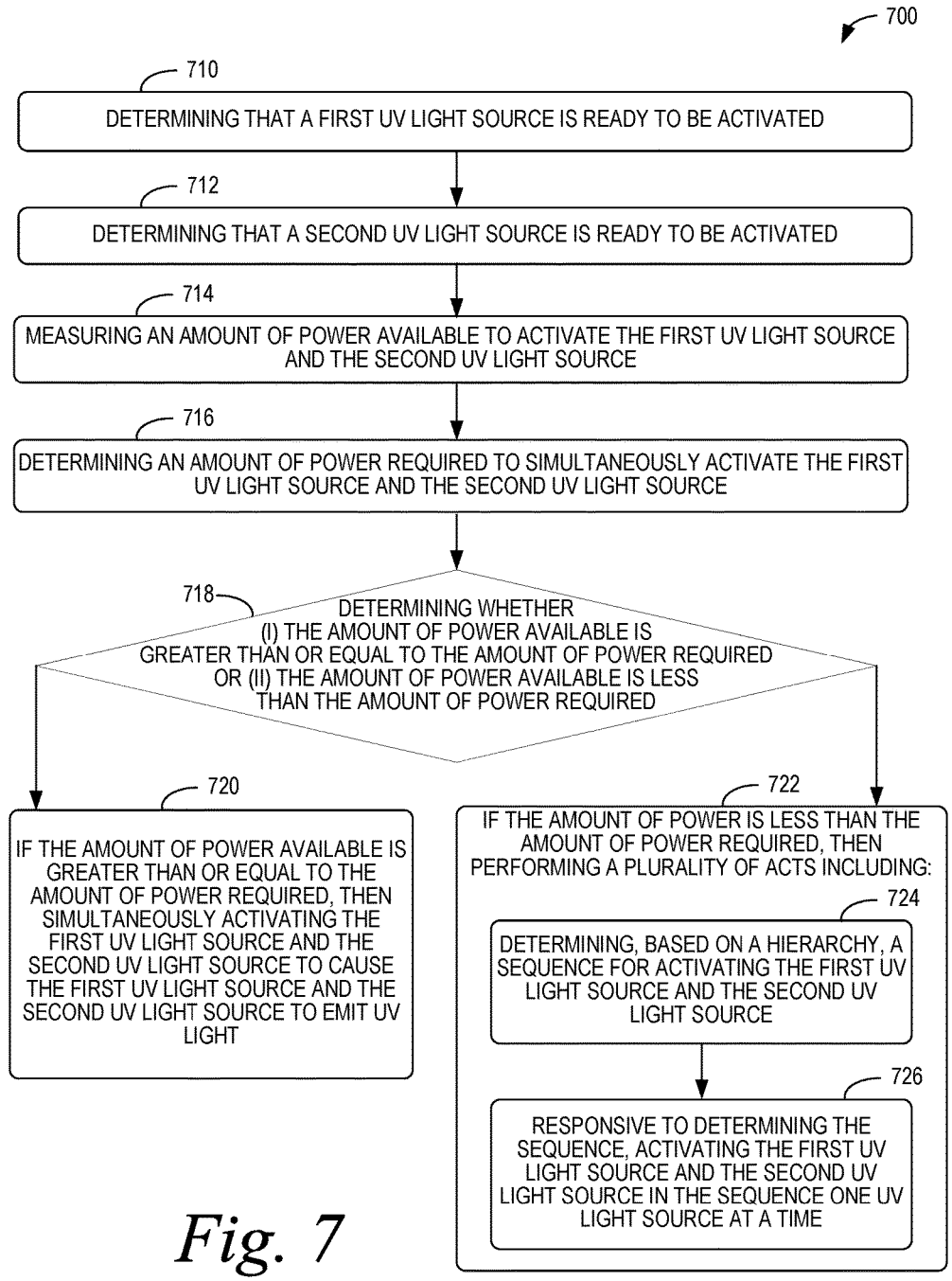
FIG. 7 illustrates a flow chart of an example process for operating a plurality of UV light sources according to an example embodiment.

Referring now to FIG. 7, a flowchart for a process 700 of operating a plurality of UV light sources is illustrated according to another example embodiment. As shown in FIG. 7, the process 700 includes determining that a first UV light source is ready to be activated at block 710, determining that a second UV light source is ready to be activated at block 712, measuring an amount of power available to activate the first UV light source and the second UV light source at block 714, and determining an amount of power required to simultaneously activate the first UV light source and the second UV light source at block 716.

At block 718, the process 700 includes determining whether (i) the amount of power available is greater than or equal to the amount of power required or (ii) the amount of power available is less than the amount of power required. If the amount of power available is greater than or equal to the amount of power required, then the process 700 includes simultaneously activating the first UV light source and the second UV light source to cause the first UV light source and the second UV light source to emit UV light at block 720.

Whereas, if the amount of power is less than the amount of power required, then the process includes performing a plurality of acts at block 722. The acts at block 722 include determining, based on a hierarchy, a sequence for activating the first UV light source and the second UV light source at block 724, and responsive to determining the sequence at block 724, activating the first UV light source and the second UV light source in the sequence one UV light source at a time at block 726.

Any of the blocks shown in FIGS. 2-7 may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In some instances, components of the devices and/or systems described herein may be configured to perform the functions such that the components are actually configured and structured (with hardware and/or software) to enable such performance. Example configurations then include one or more processors executing instructions to cause the system to perform the functions. Similarly, components of the devices and/or systems may be configured so as to be arranged or adapted to, capable of, or suited for performing the functions, such as when operated in a specific manner.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A light control system, comprising:
 a plurality of ultraviolet (UV) light sources, wherein each UV light source is configured to emit UV light when activated;
 a power sensor configured to measure an amount of power available to activate the plurality of UV light sources; and
 an activation control system in communication with the power sensor and configured to:

determine a subset of the plurality of UV light sources that are ready to be activated, indicate, in a queue stored in a data storage unit, each UV light source of the subset, arrange, in the queue and based on a hierarchy, the subset of the plurality of UV light sources in a sequence, and activate, in the sequence indicated by the queue, each UV light source of the subset by performing a plurality of acts comprising:
  (i) determining an amount of power required to activate a next UV light source in the sequence,
  (ii) determining when the measured amount of power available to activate the plurality of UV light sources is equal to or greater than the amount of power required to activate the next UV light source in the sequence,
  (iii) responsive to determining that the amount of power available is equal to or greater than the amount of power required, activating the next UV light source in the sequence, and
  (iv) repeating acts (i)-(iii) until all of the subset of UV light sources in the queue have been activated.

2. The light control system of claim 1, wherein the hierarchy comprises a set of rules based on at least one factor in a group of factors consisting of: a location of each UV light source, a size of each UV light source, an operational status of a vehicle in which each UV light source is located, an amount of time since a last activation of each UV light source, a frequency of usage of each UV light source, a frequency of usage of a respective environment disinfected by each UV light source, and an amount of power required to activate each UV light source.

3. The light control system of claim 2, wherein the plurality of UV light sources are in a plurality of lavatories of an aircraft,
  wherein, for each UV light source, the location of the UV light source comprises a class of a cabin in which the UV light source is located, and
  wherein the operational status of the vehicle comprises a phase of flight of the aircraft.

4. The light control system of claim 1, further comprising a user input device in communication with the activation control system,
  wherein the user input device is configured to receive a user input and transmit an input signal indicative of the user input to the activation control system, and
  wherein the activation control system is configured to adjust the hierarchy based on the user input indicated by the input signal.

5. The light control system of claim 1, wherein the subset comprises all of the plurality of UV light sources at a first time, and the subset comprises less than all of the plurality of UV light sources at a second time.

6. The light control system of claim 1, wherein the activation control system is configured to receive an input power from a power source and convert the input power to a supply power,
  wherein, for each UV light source of the subset, the activation control system is configured to activate the UV light source by coupling the UV light source to the supply power and decoupling a remainder of the plurality of UV light sources from the supply power, and
  wherein the power sensor is configured to sense at least one of the input power or the supply power to determine the amount of power available to activate the plurality of UV light sources.

7. The light control system of claim 1, wherein each UV light source is configured to emit the UV light at a wavelength in a range of approximately 190 nm to approximately 240 nm.

8. The light control system of claim 1, wherein the activation control system further comprises a control device in communication with the power sensor, wherein the control device is configured to:
  determine that the amount of power available is less than a total amount of power required to simultaneously activate the subset of the plurality of UV light sources, and
  determine, based on the hierarchy, the sequence responsive to the determination that the amount power available is less than the total amount of power required to simultaneously activate the subset of the plurality of UV light sources.

9. The light control system of claim 1, wherein the sequence comprises a plurality of index positions in the queue, and
  wherein one of the plurality of index positions in queue comprises two or more UV light sources in the queue, and
  wherein the activation control system is configured to simultaneously activate the two or more UV light sources.

10. The light control system of claim 1, wherein the activation control system further comprises a plurality of trigger sensors, wherein each trigger sensor corresponds to at least one of the plurality of UV light sources,
  wherein each trigger sensor is configured to detect a trigger condition for the at least one of the plurality of UV light sources corresponding to the trigger sensor and responsively generate a trigger-sensor signal indicating that the trigger condition was detected,
  wherein, to determine the subset of the plurality of UV light sources that are ready to be activated, the activation control system is configured to, for each trigger sensor corresponding to the subset of the plurality of UV light sources:
    receive the trigger-sensor signal from the trigger sensor indicating that the trigger condition was detected,
    determine, based on the trigger-sensor signal, that one or more criteria are met, and
    responsive to the determination that the one or more criteria are met, determine that the at least one UV light source corresponding to the trigger sensor is ready to be activated.

11. The system of claim 10, wherein the trigger condition comprises at least one condition selected from the group consisting of: a door of a lavatory being opened, the door of the lavatory being closed, the lavatory being occupied, and the lavatory being unoccupied, and
  wherein the one or more criteria comprises at least one criterion selected from the group consisting of: the door of the lavatory being closed, the lavatory being unoccupied, the lavatory having been occupied a predetermined number of times since a previous activation of the UV light source, and a predetermined amount of time having passed since the previous activation of the UV light source.

12. A method of operating a plurality of ultraviolet (UV) light sources, comprising:
  determining a subset of the plurality of UV light sources that are ready to be activated;
  indicating, in a queue stored in a data storage unit, each UV light source of the subset;

arranging, in the queue and based on a hierarchy, the subset of the plurality of UV light sources in a sequence;

measuring an amount of power available to activate the plurality of UV light sources; and activating, in the sequence indicated by the queue, each UV light source of the subset by performing a plurality of acts comprising:

(i) determining an amount of power required to activate a next UV light source in the sequence, (ii) determining when the measured amount of power available to activate the plurality of UV light sources is equal to or greater than the amount of power required to activate the next UV light source in the sequence, (iii) responsive to determining that the amount of power available is equal to or greater than the amount of power required, activating the next UV light source in the sequence to cause the next UV light source to emit UV light, and (iv) repeating acts (i)-(iii) until all of the subset of UV light sources in the queue have been activated.

13. The method of claim 12, wherein activating each UV light source of the subset comprises, for each UV light source of the subset:

receiving an input power from a power source;

converting the input power to a supply power;

coupling the UV light source of the subset to be activated to the supply power; and decoupling a remainder of the plurality of UV light sources from the supply power, wherein measuring the amount of power available to activate the plurality of UV light sources comprises sensing at least one of the input power or the supply power.

14. The method of claim 12, further comprising:

receiving, via a user input device, a user input; and adjusting, based on the user input, the hierarchy.

15. The method of claim 12, further comprising:

determining that the amount of power available is less than a total amount of power required to simultaneously activate the subset of the plurality of UV light sources, and determining, based on the hierarchy, the sequence responsive to the determination that the amount power available is less than the total amount of power required to simultaneously activate the subset of the plurality of UV light sources.

16. The method of claim 12, wherein the hierarchy comprises a set of rules based on at least one factor in a group of factors consisting of: a location of each UV light source, a size of each UV light source, an operational status of a vehicle in which each UV light source is located, an amount of time since a last activation of each UV light source, a frequency of usage of each UV light source, a frequency of usage of an environment disinfected by each UV light source, and/or an amount of power required to activate each UV light source.

17. The method of claim 16, wherein the plurality of UV light sources are in a plurality of lavatories of an aircraft, wherein, for each UV light source, the location of the UV light source comprises a class of a cabin in which the UV light source is located, and wherein the operational status of the vehicle comprises a phase of flight of the aircraft.

18. The method of claim 12, wherein each UV light source is in a respective lavatory of a vehicle, and wherein determining a subset of the plurality of UV light sources that are ready to be activated comprises, for each UV light source of the subset, determining at least one of: (i) a door of the respective lavatory being closed, (ii) the respective lavatory being unoccupied, (iii) the respective lavatory having been occupied a predetermined number of times since a previous activation of the UV light source, and (iv) a predetermined amount of time having passed since the previous activation of the UV light source.

19. A method of operating a plurality of ultraviolet (UV) light sources, comprising:

determining that a first UV light source is ready to be activated;

determining that a second UV light source is ready to be activated;

measuring an amount of power available to activate the first UV light source and the second UV light source;

determining an amount of power required to simultaneously activate the first UV light source and the second UV light source;

determining whether (i) the amount of power available is greater than or equal to the amount of power required or (ii) the amount of power available is less than the amount of power required;

if the amount of power available is greater than or equal to the amount of power required, then simultaneously activating the first UV light source and the second UV light source to cause the first UV light source and the second UV light source to emit UV light; and if the amount of power is less than the amount of power required, then performing a plurality of acts comprising:

indicating, in a queue stored in a data storage unit, the first UV light source and the second UV light source, arranging, in the queue and based on a hierarchy, the first UV light source and the second UV light source in a sequence, and responsive to determining the sequence, determining that the amount of power available is greater than or equal to an amount of power required to activate the first UV light source, responsive to determining that the amount of power available is greater than or equal to the amount of power required to activate the first UV light source, activating the first UV light source in the sequence, after activating the first UV light source, determining that the amount of power available is greater than or equal to an amount of power required to activate the second UV light source, and responsive to determining that the amount of power available is greater than or equal to the amount of power required to activate the second UV light source, activating the second UV light source in the sequence.

20. The method of claim 19, wherein the hierarchy comprises a set of rules based on at least one factor in a group of factors consisting of: a location of each UV light source, a size of each UV light source, an operational status of a vehicle in which each UV light source is located, an amount of time since a last activation of each UV light source, a frequency of usage of each UV light source, a frequency of usage of an environment disinfected by each UV light source, and/or an amount of power required to activate each UV light source.

* * * * *